United States Patent
Ritter (10) Patent No.: US 10,888,647 B2
(45) Date of Patent: Jan. 12, 2021

(54) DEVICE FOR EXTRACORPOREAL BLOOD TREATMENT COMPRISING AN IMPROVED ARRANGEMENT OF A BLOOD TREATMENT DEVICE

(71) Applicant: B. BRAUN AVITUM AG, Melsungen (DE)

(72) Inventor: Kai-Uwe Ritter, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 27 days.

(21) Appl. No.: 16/021,945

(22) Filed: Jun. 28, 2018

(65) Prior Publication Data
US 2019/0001041 A1 Jan. 3, 2019

(30) Foreign Application Priority Data
Jun. 29, 2017 (DE) .................. 10 2017 114 528

(51) Int. Cl.
*A61M 1/14* (2006.01)
*A61M 1/16* (2006.01)
(Continued)

(52) U.S. Cl.
CPC ............ *A61M 1/1652* (2014.02); *A61M 1/14* (2013.01); *A61M 1/165* (2014.02); *A61M 1/262* (2014.02);
(Continued)

(58) Field of Classification Search
CPC .. A61M 1/1652; A61M 1/367; A61M 1/3403; A61M 1/3643; A61M 1/14;
(Continued)

(56) References Cited

U.S. PATENT DOCUMENTS 5,770,064 A * 6/1998 Jonsson .............. A61M 1/1652
210/232
6,277,277 B1 8/2001 Jacobi et al.
(Continued)

FOREIGN PATENT DOCUMENTS

CA 2759590 A1 10/2010
DE 19925297 C1 7/2000
(Continued)

OTHER PUBLICATIONS

European Search Report for European Application No. 18178856.3, dated Nov. 27, 2018 with unchecked machine translation, 12 pages.
(Continued)

*Primary Examiner* — Angel Olivera (57) ABSTRACT

A device for extracorporeal blood treatment, in particular a dialysis device, including an internal fluidic system for a treatment liquid, in particular for a dialysis liquid, the internal fluidic system having at least two liquid connectors for connecting a substantially cylindrical filter element, in particular a dialyzer, to the internal fluidic system for passing a treatment liquid through the filter element, and including a mounting for exchangeably holding the filter element in such a way that the filter element can be connected to the liquid connectors of the internal fluidic system and to an extracorporeal blood line in an intended manner, wherein the mounting for holding the filter element is designed in such a way that a cylinder longitudinal axis of the filter element is substantially horizontally aligned.

13 Claims, 5 Drawing Sheets

(51) Int. Cl.
- *A61M 5/14* (2006.01)
- *B01D 61/30* (2006.01)
- *A61M 1/26* (2006.01)
- *A61M 1/34* (2006.01)
- *A61M 1/36* (2006.01)
- *B01D 24/46* (2006.01)

(52) U.S. Cl.
CPC ............ *A61M 1/34* (2013.01); *A61M 1/3403* (2014.02); *A61M 1/3606* (2014.02); *A61M 1/367* (2013.01); *A61M 1/3643* (2013.01); *A61M 1/3649* (2014.02); *A61M 5/1417* (2013.01); *B01D 24/4673* (2013.01); *A61M 1/168* (2013.01); *A61M 1/1654* (2013.01); *A61M 1/265* (2014.02); *A61M 1/369* (2013.01); *A61M 2209/082* (2013.01); *B01D 61/30* (2013.01); *B01D 2201/4023* (2013.01)

(58) Field of Classification Search
CPC .............. A61M 1/1654; A61M 1/3606; A61M 1/3649; A61M 1/165; B01D 2201/4023; B01D 61/30; B01D 24/4673
See application file for complete search history.

(56) References Cited

U.S. PATENT DOCUMENTS

| | | |
|---|---|---|
| 9,579,438 B2 | 2/2017 | Haecker et al. |
| 2016/0022894 A1* | 1/2016 | Jensen ................ A61M 1/3644 210/646 |
| 2016/0074565 A1 | 3/2016 | Giordano et al. |

FOREIGN PATENT DOCUMENTS

| | | | |
|---|---|---|---|
| DE | 69625279 T2 | 4/2003 | |
| EP | 0747074 A1 | 12/1996 | |
| EP | 2942070 A2 * | 11/2015 | ............. A61M 1/16 |
| WO | 2004028594 A1 | 4/2004 | |
| WO | 2010121821 A1 | 10/2010 | |

OTHER PUBLICATIONS

German Search Report for German Application No. 10 2017 114 528.1, dated Jan. 30, 2018, with translation, 13 pages.

\* cited by examiner

DEVICE FOR EXTRACORPOREAL BLOOD TREATMENT COMPRISING AN IMPROVED ARRANGEMENT OF A BLOOD TREATMENT DEVICE

CROSS REFERENCE TO RELATED APPLICATIONS

This application claims priority to German application DE 10 2017 114 528.1 filed Jun. 29, 2017, the contents of such application being incorporated by reference herein.

FIELD OF THE INVENTION

The invention relates to an apparatus for extracorporeal blood treatment, in particular a dialysis device, comprising an internal fluidic system for a treatment liquid, said internal fluidic system having at least two liquid connectors for connecting a substantially cylindrical filter element to the internal fluidic system for passing a treatment liquid through the filter element, and comprising a mounting for exchangeably holding the filter element in such a way that the filter element can be connected to the liquid connectors of the internal fluidic system and to an extracorporeal blood line in the intended manner.

BACKGROUND OF THE INVENTION

From the prior art, devices for extracorporeal blood treatment are generally known. Such devices or machines are designed for permanent use and are usually equipped with exchangeable blood treatment units designed and intended as single-use articles (one-use articles, disposable articles). Examples of such blood treatment units are filter elements and in particular dialyzers.

As a rule, the blood treatment units have an essentially cylindrical shape. In known devices for extracorporeal blood treatment, such as those shown in FIGS. 1 to 6, the blood treatment units for blood treatment are arranged or are being arranged on the device in a substantially vertical operating position and are fluidically connected or can be fluidically connected to its internal fluidic system and to the extracorporeal blood line. A substantially vertical operating position is such a position of the cylindrical blood treatment unit in which the longitudinal axis of the cylinder is substantially vertically aligned. For the purpose of holding the blood treatment unit on a known device, it has a mounting, for example in the form of two clamping jaws or arms, between which the blood treatment unit can be inserted with its cylinder longitudinal axis in a substantially vertical position and held by clamps. The mounting and the blood treatment unit are matched with each other in such a way that the insertion and removal of the blood treatment unit is simple and easy. However, there is the particular disadvantage that the blood treatment unit may slip in the mounting and a desired intended position relative to the device is not always ensured. In order to ensure safe and trouble-free treatment despite such positional variations, the blood treatment units and the internal fluidic system of the device are fluidically connected to each other with longer flexible hose segments. Although this prevents unintentional detachment of the hose segments from the internal fluidic system and/or the blood treatment unit, said longer hose segments lead to undesirable temperature losses, both in the treatment liquid contained therein and in the blood contained in the extracorporeal blood line. In addition, long hose segments lead to a situation at the device that is difficult to understand for an operator, so that incorrect connections and at least more difficult usage situations can occur.

SUMMARY OF THE INVENTION

Based on the prior art described above, the present invention is based on the task of eliminating the disadvantages mentioned above, in particular to design a device for extracorporeal blood treatment in such a way that a safe and simple replacement of a blood treatment unit may even be possible with one hand, the blood treatment unit can be held securely in position on the device and temperature changes and in particular temperature losses in hose lines connected to the blood treatment unit can be avoided or at least minimized as far as possible.

According to aspects of the invention, an object is achieved by a device for extracorporeal blood treatment, in particular a dialysis device, comprising an internal fluidic system for a treatment liquid, in particular for a dialyzing fluid, said internal fluidic system having at least two liquid connectors for connecting a substantially cylindrical filter element, in particular a dialyzer, to the internal fluidic system for passing treatment liquid through the filter element, and comprising a mounting for exchangeably holding the filter element in such a way that the filter element can be connected to the liquid connectors of the internal fluidic system and to an extracorporeal blood line in the intended manner, wherein the mounting for holding the filter element is designed in such a way that its cylinder longitudinal axis is substantially horizontally aligned. The device may also include a blood pump for conveying blood between a venous connector and an arterial connector of the extracorporeal blood line through the filter element.

It should be noted here that the term "internal fluidic system" refers to that part of the fluid-carrying line sections which is arranged upstream or downstream of such connectors which are preferably fixed to the housing and to which hose lines (in one-way design) are connected that are directly coupled to the dialyzer.

An example of a filter element that can be arranged or is arranged on the device is a conventional dialyzer, for example a tube bundle dialyzer. The filter element preferably has an essentially cylindrical shape. It may be provided with end caps arranged at both sides at the ends of a cylindrical center section and with connectors for treatment liquid/dialysis liquid and blood positioned in both axial end regions of the center section. The device according to aspects of the invention can be set up and suitable for receiving the filter element or for being equipped with it. Alternatively, it can include the essentially cylindrical, replaceable filter element, in particular in the form of a dialyzer. The filter element may have a blood connector and a treatment liquid connector on each of its two end-side sections (adjacent to the end faces of the cylinder), in particular a blood inlet, a blood outlet, a treatment liquid inlet and a treatment liquid outlet. The blood inlet and outlet are located on opposite sides of the filter element. The treatment liquid inlet and outlet are also located on opposite sides of the filter element. The filter element can be operated in the co-current and/or preferably in the countercurrent mode. An essentially cylindrical filter element in the sense of the invention also includes in particular a filter element which has a cross-sectional shape deviating from the circular shape, for example an oval cross-section or a square or polygonal cross-section, also rectangular cross-section.

The mounting can also referred to as a bracket. The device can have one or more mountings, in each case for one filter element or several filter elements. According to aspects of the invention, the mounting is designed in such a way that a filter element is received/held/aligned essentially horizontally, i.e. rests quasi on or in the mounting and is supported at least from below. In this way, the filter element can be positioned in a non-displaceable manner in the mounting and on the device by gravity. Compared to the prior art described above, the invention enables a more stable positional arrangement and mounting of the filter element on the device. The line segments connecting the filter element to the internal fluidic system, such as e.g. hose segments, can therefore be shorter than in prior art, especially as short as possible, since no inaccurate positioning or change in position of the filter element on the device has to be compensated. Due to the reduced length of the line segments, temperature fluctuations, in particular a cooling down of liquids (dialysate, blood) flowing therein can be minimized or even avoided. A further advantage of the short line segments is that a better overview for an operator can be created on the device, as for example line loops and clutter can be prevented.

A substantially horizontal position in the sense of the invention also includes positions deviating from the exact horizontal position by a small angle or inclined positions. A small angle is in particular such an angle that is sufficient to allow treatment liquid and/or blood in the filter element to flow in a preferred direction and be better removed, but still ensures a positionally stable reception of the filter element. The inclination of the filter element is always less than 10°.

Advantageous embodiments of the invention are claimed in the subclaims and are explained in more detail below.

Preferably, the internal fluidic system comprises liquid connectors in the form of treatment liquid connectors, especially dialysate liquid connectors, and flushing connectors. In particular, the internal fluidic system may have a connector for the supply of treatment/dialyzing liquid, a connector for the discharge of treatment/dialyzing liquid and at least two flushing connectors. At least one or all of the connectors can be provided in the form of quick-release couplings, for example in the form of a Hansen connector or a Luer-lock connector. In particular, the connectors may be firmly integrated in a housing of the device, in particular in a housing front. According to a particularly advantageous embodiment, the connectors each have a coupling with automatic closure, so that the internal fluidic system is sealed without leakage and protected against soiling when the filter element is not connected and unwanted leakage of treatment liquid can be avoided.

One embodiment of the invention is characterized in that the mounting has at least one substantially horizontally aligned contact surface for the filter element. The contact surface can be designed in particular as a support surface and/or clamping surface.

The mounting may comprise at least one clamping device for holding a filter element or be designed in the form of a clamping device. In particular, it can have two opposing, preferably spring-elastic clamping arms or clamping jaws between which the mounting space for the filter element is formed. The clamping arms or jaws can be made of plastic or stainless steel, for example. They preferably have an inner contour matching the outer contour of the filter element. They can also encircle a part of the circumference of the filter element and thus ensure that the filter element is held securely in place as intended.

Alternatively, the mounting can be essentially fork-shaped. In particular, it can be provided with two upwardly facing, opposing fork arms, between which the preferably upwardly open receiving space for the filter element is formed. The filter element can be placed particularly easily on such a fork-shaped mounting and is nevertheless always in a defined position relative to the device.

In the sense of the invention, the mounting is preferably designed in such a way that filter elements of different length and/or cross-sectional width/diameter can be accommodated and held therein. According to aspects of the invention, this is achieved in particular by providing a mounting open on one side with a continuously widening width toward its opening or by providing correspondingly shaped spring-elastic clamping arms or clamping jaws.

Preferably, the mounting is designed in such a way that the filter element is held in it at a defined position on the device, but can be rotated about its longitudinal axis. In this way, the filter element can be placed in different rotary positions in the mounting: For example, it may be positioned such that at least one of its liquid connectors points upwards to assist venting of the filter element during filling. In addition, the filter element can be rotated or positioned for emptying in such a way that at least one of its liquid connectors points downwards, so that the draining of liquid from the filter elements is facilitated and/or liquid can largely drain off or be sucked off completely. Regardless of the position with regard to rotation about its longitudinal axis, the filter element is always held according to aspects of the invention in fixed position relative to the device by the mounting acting on it from below.

According to one embodiment, the mounting can be pivoted on the device, in particular about a horizontal axis. This axis is preferably aligned essentially orthogonally to the longitudinal axis of the filter element. The angular range in which the mounting can be swiveled, for example, can be in a range of approx. ±5°, preferably of approx. ±2°, more preferably of approx. ±1° and most preferably of approx. +0.5°. The mounting can be swiveled from the horizontal to only one or both directions, the horizontal being defined as a swiveling angle of 0°. The angle of inclination of the essentially horizontally arranged longitudinal axis of the filter element can be adjusted with such a swiveling mounting, thus varying the flow characteristics of the filter element. For example, it can be inclined for filling and/or emptying and positioned horizontally during treatment.

The mounting can also provide for the dialyzer to be brought into a vertical position. This may be necessary if dialyzers are to be used that would not support filling with liquid in the horizontal position or therapy in the horizontal position.

The mounting can also be coupled to a drive to drive it to swivel around the horizontal. The inclined positioning of the filter element can be automated and machine-controlled in this way. In addition, the mounting may be preloaded in or against the direction of rotation around the horizontal. This can be achieved in particular with a spring element or similar. For example, the preload can act in such a way that the filter element is returned from an inclined position to the horizontal, so that this non-tilt position is preferably assumed as soon as the filter element is no longer urged into an inclined position.

In one embodiment of the invention, the device may comprise flexible conduit sections for connecting the liquid connectors of the internal fluidic system to the blood connectors and the treatment liquid connectors of the filter element. The liquid connectors of the internal fluidic system are connected or can be connected to the flexible line sections. Such flexible line sections or segments may take the form of hose lines known per se in the field of extracorporeal blood treatment.

It is of particular advantage if the liquid connectors of the internal fluidic system are positioned relative to the filter element such and the length of the flexible line sections to be connected to the filter element is such that an intended connection of the filter element is ensured, but an improper connection of the filter element is impossible due to an insufficient length of the flexible line sections. Alternatively or additionally, it is of particular advantage if the liquid connectors of the internal fluidic system are positioned in such a way relative to the filter element, and the length of the flexible line sections to be connected to the filter element is in each case such that an intended connection of the liquid connectors to each other is ensured during flushing the internal fluidic system, but an improper connection of the liquid connectors to each other during flushing the internal fluidic system is impossible due to an insufficient length of the flexible line sections. This increases the operating safety of the device in an advantageous way and avoids possible treatment errors due to faulty connection of the filter element on the device. For example, the treatment liquid connectors of the internal fluidic system are preferably located in a housing front of the device. In addition, flushing connectors may be located in the housing front of the device. Preferably, the treatment liquid connectors of the internal fluidic system are placed near the corresponding connectors of the filter element. The flushing connectors are preferably located near the treatment liquid connectors of the internal fluidic system and are relatively far apart. It is particularly advantageous if the distance between the flushing connectors and the treatment liquid connector to be fluidically connected to them during a flushing process is smaller than the distance between two flushing connectors. Preferably, the flushing connectors are so far apart that it is not possible to put them together in a wrong manner, i.e. to incorrectly connect the flushing connector to the treatment liquid connector. It is also essential for this that the length of line segments for the fluidic connection of the internal fluidic system to the filter element and of the flushing connectors of the internal fluidic system to the treatment liquid connectors of the internal fluidic system is dimensioned such that no incorrect connection can be established, i.e. that the line segments are sufficiently short. For example, the line segments may have any length between about 10 cm and about 30 cm.

In summary, it can be said that especially the following advantages and improvements can be achieved by aspects of the invention:
- Significantly improved handling, the dialyzer is clicked in place at the front and does not slip down any longer
- One-handed setup of the dialyzer is possible
- Very short blood lines, thus reduced blood volume in the hose
- Improved biocompatibility
- Lower costs of the blood hose
- Very simple and cost-effective design of the dialyzer mounting is possible
- Low temperature/energy loss at the DF lines
- Improved temperature accuracy at the dialyzer
- Reduced disinfection time
- Less room heating
- Energy saving

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

FIGS. 1 to 6 each show a prior art dialysis machine 1 as an example of a device 1 for extracorporeal blood treatment with an exchangeably arranged filter element 2 in the form of a dialyzer 2 which is fluidically connected to and exchangeably arranged on an internal fluidic system not shown in the Figures. In all known devices 1 which are shown, the dialyzer 2 is arranged in each case substantially vertically on a housing 4 of the device 1 by means of a mounting 3 in such a way that its longitudinal axis 5 drawn into the Figures is substantially vertically aligned.

Figure 1:
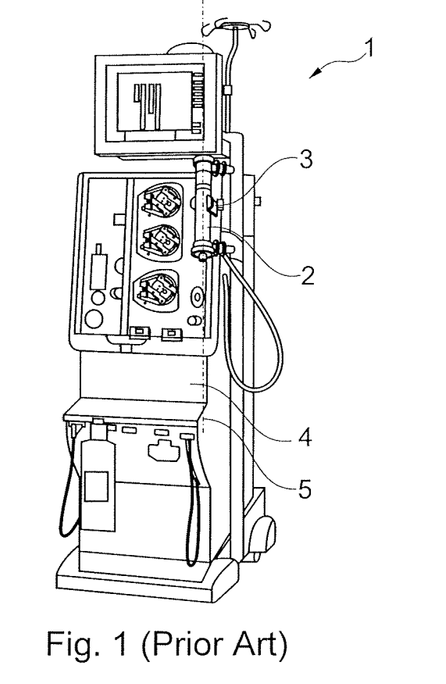
FIG. 1 is a view of a known device for extracorporeal blood treatment.
Figure 2:
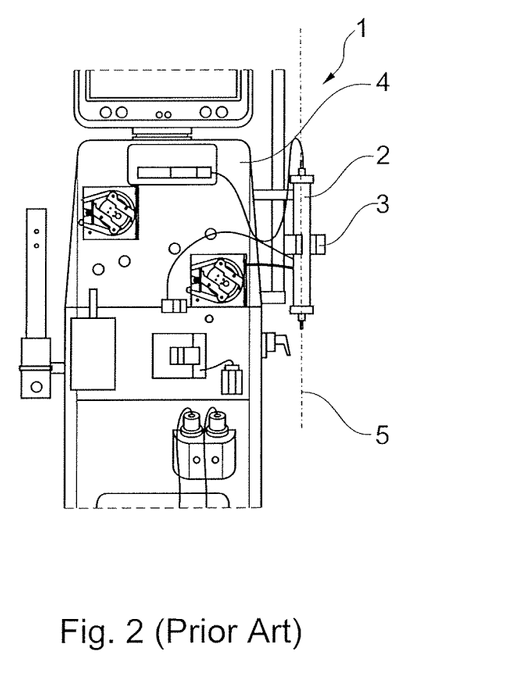
FIG. 2 is a view of another known device for extracorporeal blood treatment.
Figure 3:
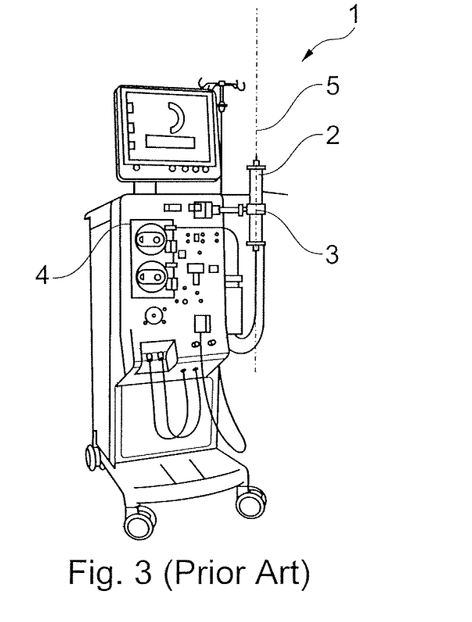
FIG. 3 is a view of another known device for extracorporeal blood treatment.
Figure 4:
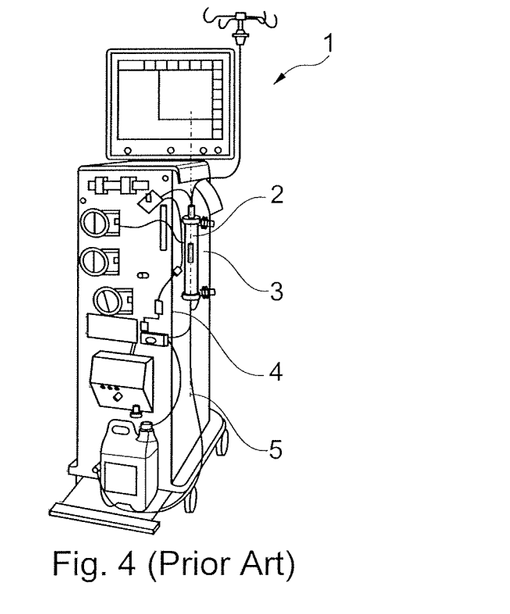
FIG. 4 is a view of another known device for extracorporeal blood treatment.
Figure 5:
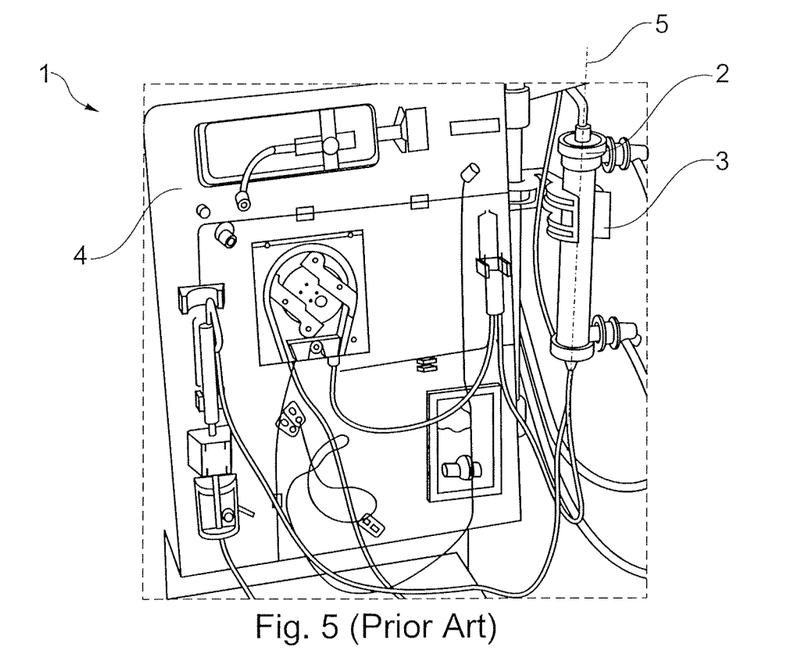
FIG. 5 is a view of another known device for extracorporeal blood treatment.
Figure 6:
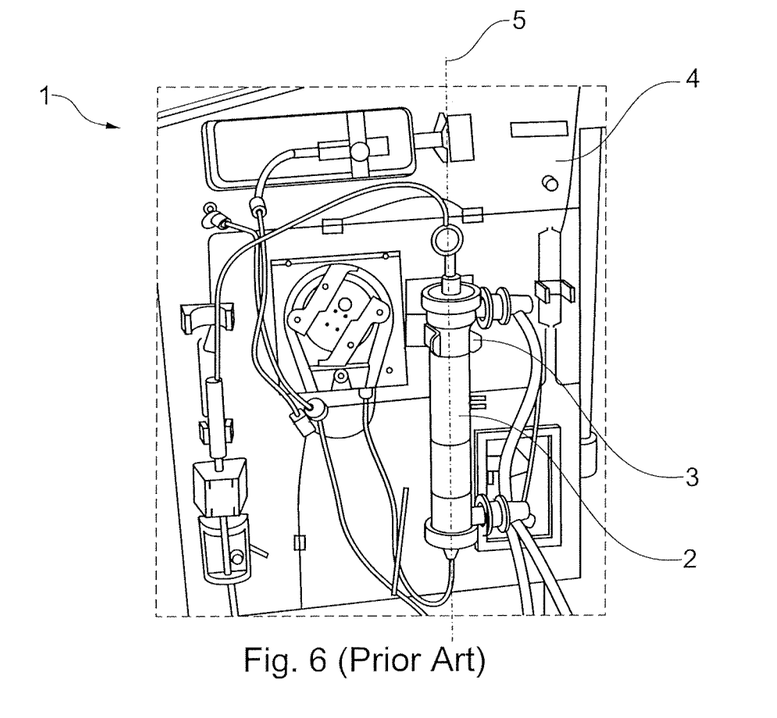
FIG. 6 is a view of another known device for extracorporeal blood treatment.
Figure 7:
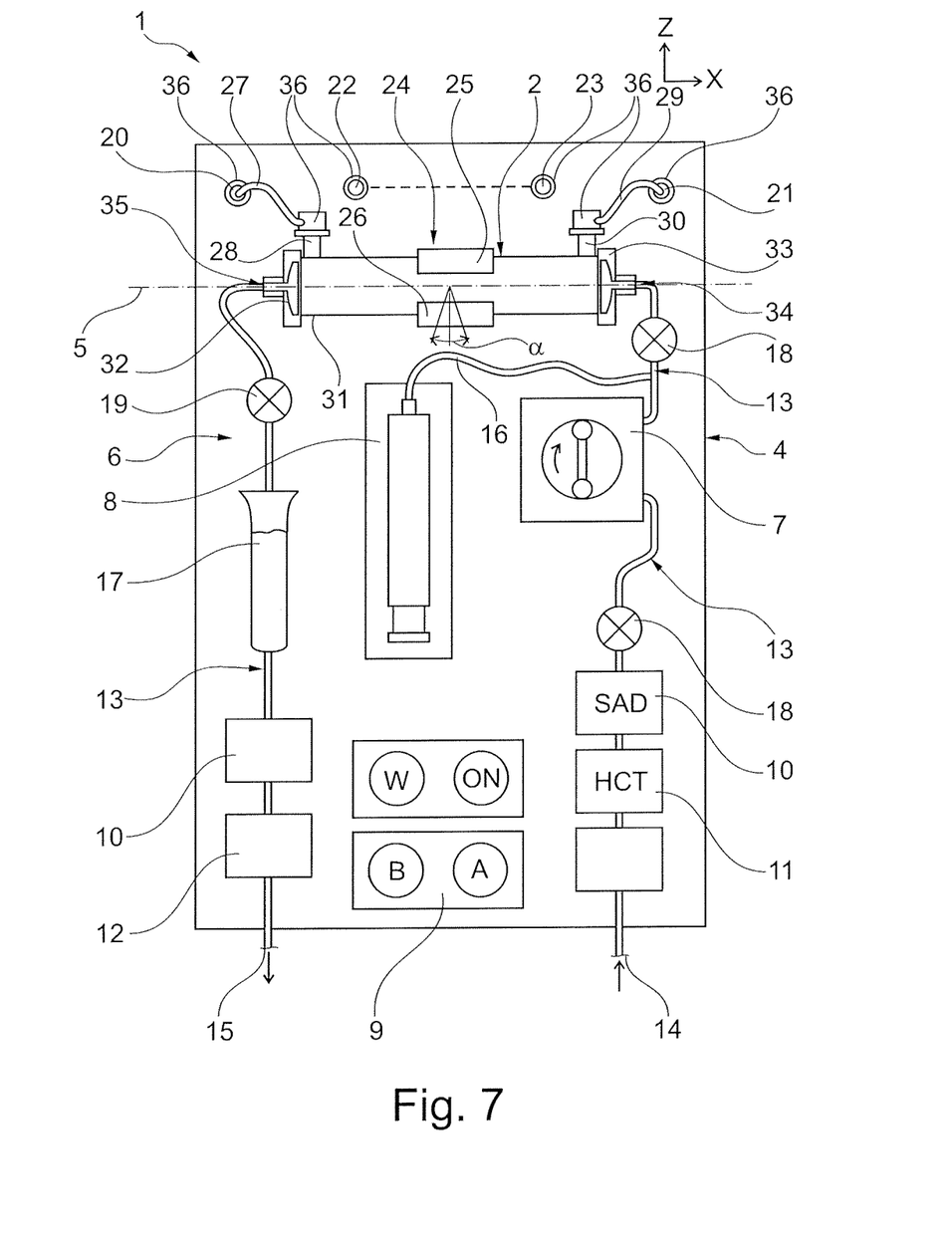
FIG. 7 is a schematic view of a housing front of a device according to aspects of the invention.

FIG. 7 shows in a schematic elevation view an arrangement of the filter element/dialyzer 2 on a front 6 of a housing 4 of a device 1 according to aspects of the invention. FIG. 7 shows the horizontal X and the vertical Z for better orientation. The housing front 6 forms a kind of operating surface or operating space, quasi as an interface between a user/operator and the machine. In addition to the dialyzer 2, a blood pump 7, a heparin pump 8, a concentrate receptacle 9, one or two air sensors 10, a hematocrit sensor 11 and a venous hose shut-off clamp (SAKV), and possibly an arterial hose shut-off clamp (SAKA) 12 are accessible to the user at the front. FIG. 7 also shows an extracorporeal blood line 13 comprising an arterial connector 14 and a venous connector 15. As indicated in FIG. 7, the extracorporeal blood line 13 is inserted into the blood pump 7, here in the form of a peristaltic pump 7, so that the blood pump 7 transports blood from the arterial connector 14 to the venous connector 15. The heparin pump 8 is fluidically connected to the extracorporeal blood line 13 via a heparin line 16. In addition, an air bubble trap 17, two arterial pressure sensors 18 and a venous pressure sensor 19 are integrated in the blood line 13.

The internal fluidic system (not shown in FIG. 7) of the device 1 is arranged and hidden behind the housing front 6. A treatment liquid connector 20 for the supply of a treatment/dialysis liquid, a treatment liquid connector 21 for the discharge of a treatment/dialysis liquid and two flushing connectors 22, 23 are integrated or installed in the housing front 6. A mounting 24 for the filter element 2 is also located in its vicinity. Said mounting is designed as a clamping device and comprises a first clamping arm 25 and a second clamping arm 26, which form a mounting space between them for the filter element 2. The clamping arms 25, 26 are each made of plastic and have claw-like end sections with retaining, contact or support surfaces 38 facing the filter element 2 and with spring elastic properties in a direction transverse to the longitudinal axis 5 of filter element 2. The contact surface 38 is aligned so as to be essentially parallel to the longitudinal axis 5 of the cylinder. The filter element 2 can thus be inserted into the receiving space between the clamping arms 25, 26 in a manner known per se under elastic deformation and is held in the claw-like end sections by their elastic re-deformation.

FIG. 7 clearly shows that the longitudinal axis 5 of the filter element 2 arranged and held in the mounting 24 is essentially horizontally aligned. As a result of the mounting in the claw-like end sections of the clamping arms 25, 26 on or at their support surfaces 38, it can be rotated about its cylinder longitudinal axis 5. In addition, the mounting 24 can be rotated in an inclination angle range a about a swivel axis that is aligned orthogonally to the longitudinal axis 5 and in FIG. 7 orthogonally to the drawing plane. The angle of inclination a is within an angle range of approx. ±5° around the horizontal, preferably of approx. ±2° around the horizontal, preferably of approx. ±1° around the horizontal, most preferably of approx. ±0.5° around the horizontal, wherein at an angle of inclination of 0° the longitudinal axis 5 is aligned exactly in the horizontal.

The filter element 2 has a substantially cylindrical shape and comprises a cylindrical central section 31 on both ends of which end caps 32, 33 are arranged, which form a blood inlet 34 and a blood outlet 35. A dialysate input 28 is formed in the left axial end section of the middle section 31 and a dialysate output 30 is formed in the right axial end section of the middle section 31.

FIGS. 8 to 13 are described by way of example using a dialysis device 1 with a dialyzer 2 as filter element and dialysate as treatment liquid. Other treatment applications are in the field of the invention.

Figure 8:
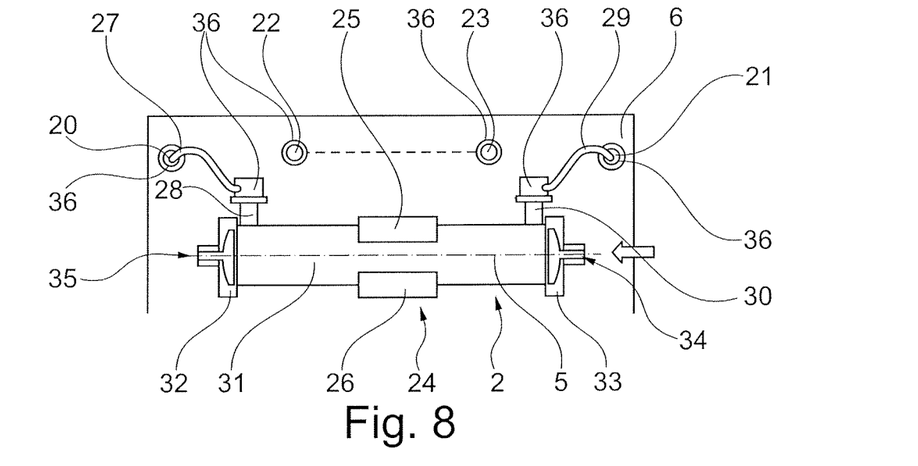
FIG. 8 is a schematic partial view of a device according to aspects of the invention with a filter element taken up during therapy or a priming process.

FIG. 8 shows a schematic representation of a filter element incorporated according to aspects of the invention during a therapy or a priming process. The dialysate connector 20 for the supply of dialysis liquid, the dialysate connector 21 for the discharge of dialysis liquid and the two flushing connectors 22, 23 are each arranged near and above filter element 2. As shown in the Figure, the two flushing connectors 22, 23 are fluidically connected inside by means of a line 37, which is part of the internal fluidic system. The dialysate connector 20 for the supply of dialysis liquid is fluidically connected to the dialysate input 28 of filter element 2 by means of a first line segment/connecting hose/hose segment 27. The dialysate connector 21 for the discharge of dialysis liquid is fluidically connected to the dialysate outlet 30 of filter element 2 by means of a second line segment/connecting hose/hose segment 29. The hose segments 27, 29 are attached to the respective liquid connectors 20, 21 by means of quick-release couplings 36. Their lengths and the arrangement of the dialysate connector 20 for the supply of dialysate fluid, the dialysate connector 21 for the discharge of dialysate liquid and the two flushing connectors 22, 23 are such that the hose segment 27 can only connect the dialysate connector 20 to the flushing connector 22, but not the dialysate connector 20 to the flushing connector 23. Similarly, the hose segment 29 can only connect the dialysate connector 21 to the flushing connector 23, but not the dialysate connector 21 to the flushing connector 22. In FIG. 8, the dialysate flows through the filter element 2 from left to right and blood flows from right to left, i.e. in countercurrent operation.

Figure 9:
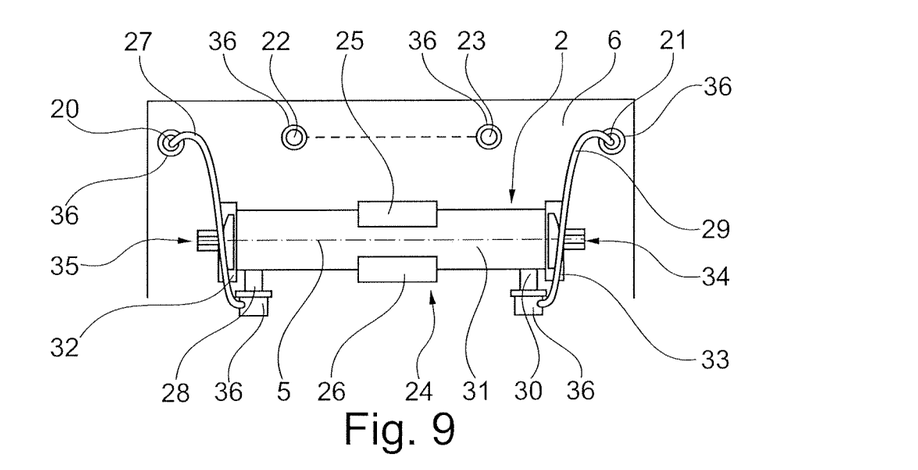
FIG. 9 is a schematic partial view of a device according to aspects of the invention with a filter element received during emptying.

FIG. 9 shows a schematic representation during emptying the filter element. The filter element 2 is fluidically connected to the internal fluidic system of the device as described in FIG. 8. However, compared to the representation of FIG. 8, it is rotated by about 180° about its longitudinal axis 5, so that the dialysate inlet 28 and the dialysate outlet 30 point downwards and facilitate the outflow of dialysate from filter element 2 and thus its emptying.

Figure 10:
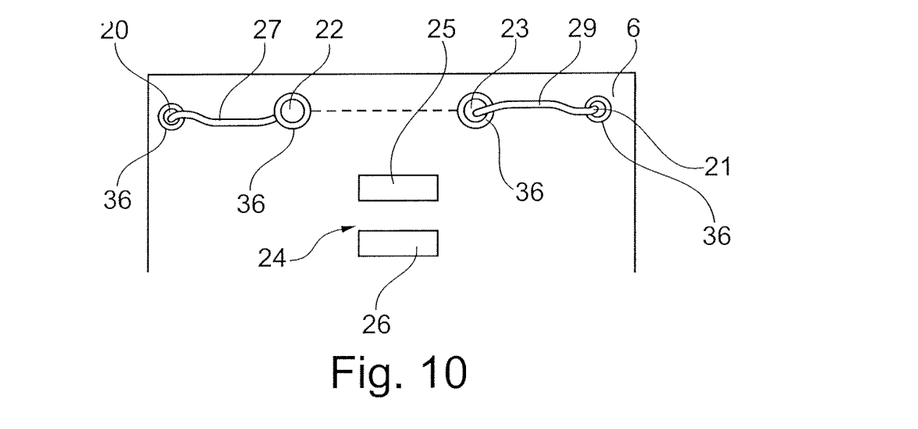
FIG. 10 is a schematic partial view of a device according to aspects of the invention during disinfection.

FIG. 10 shows a schematic representation of a device according to aspects of the invention during a disinfection of the internal fluidic system. The filter element 2 is decoupled from the internal fluidic system and removed from the mounting 24. The hose segment 27 is attached to the flushing connector 22 so that the latter is connected to the dialysate connector 20. The hose segment 29 is attached to the flushing connector 23 so that the latter is connected to the dialysate connector 21.

Figure 11:
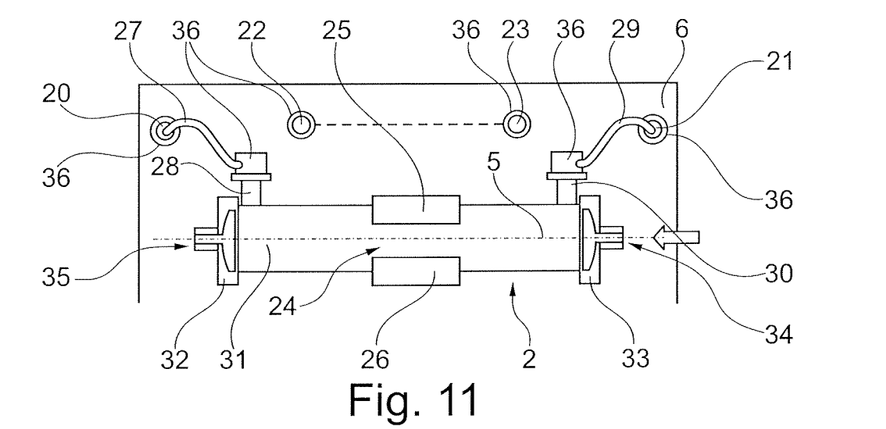
FIG. 11 is a schematic partial view of a device according to aspects of the invention with received filter element comprising a first arrangement of liquid connectors on the device in the context of the invention.
Figure 12:
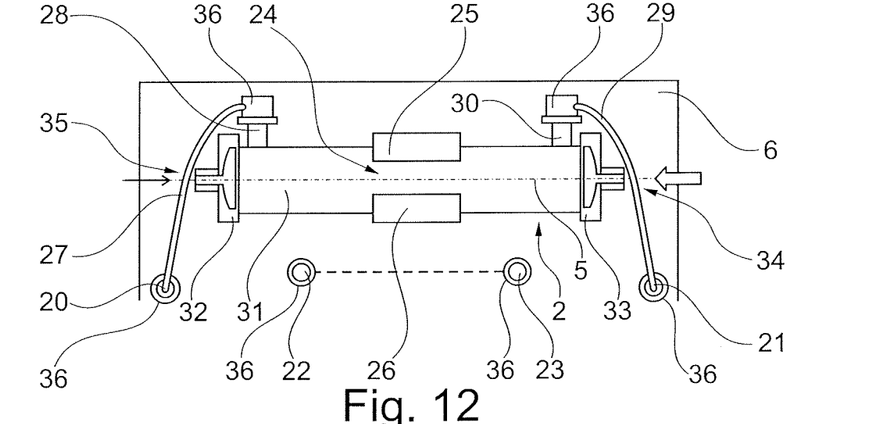
FIG. 12 is a schematic partial view of a device according to aspects of the invention with received filter element comprising a second arrangement of liquid connectors on the device in the context of the invention.
Figure 13:
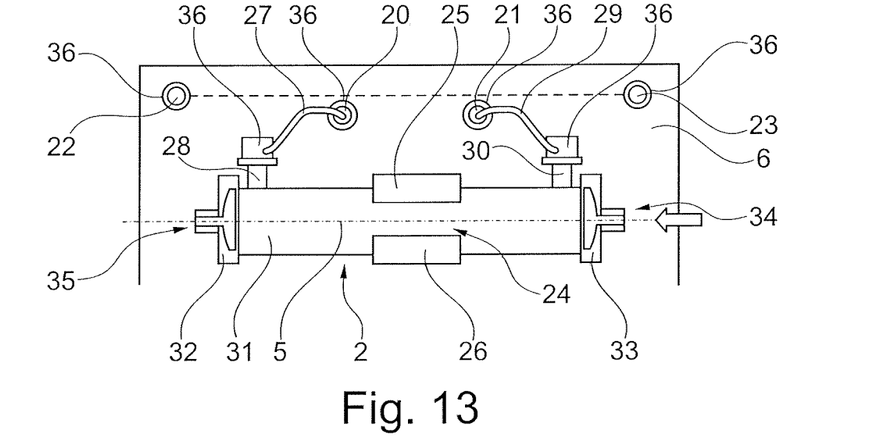
FIG. 13 is a schematic partial view of a device according to aspects of the invention with received filter element comprising a third arrangement of liquid connectors on the device in the context of the invention.

FIG. 11, FIG. 12 and FIG. 13 each show the arrangement of liquid connectors on the device relative to filter element 2 in a schematic diagram. In the embodiment of FIG. 11, both the dialysate connectors 20 and 21 and the flushing connectors 22, 23 are arranged above the mounting 24, see also the description in FIG. 8. FIG. 12 shows an alternative arrangement in which both the dialysate connectors 20 and 21 as well as the flushing connectors 22, 23 are arranged below the mounting 24. In both variants, the flushing connectors 22, 23 are located between dialysate connectors 20 and 21. FIG. 13 shows another variant in which both the dialysate connectors 20 and 21 and the flushing connectors 22, 23 are arranged above the mounting 24, but different from the design of FIG. 11, the flushing connectors 22, 23 are arranged outside and the dialysate connectors 20 and 21 inside between the flushing connectors 22, 23. All embodiments have in common that an incorrect connection of the hose segments 27, 29, as described above with reference to FIG. 8, is not possible.

The invention claimed is:

1. A device for extracorporeal blood treatment, the device comprising:
    a housing having an internal fluidic system for a treatment liquid, a first housing liquid connector, and a second housing liquid connector, the first and second housing liquid connectors configured to convey a treatment liquid through the internal fluidic system, the housing further comprising a front operating surface forming a user interface;
    a cylindrical filter element that extends along a cylinder longitudinal axis from a first end to a second end and has a first treatment liquid connector at the first end and a second treatment liquid connector at the second end;
    a mounting configured to hold the cylindrical filter element, wherein the mounting is oriented such that a cylinder longitudinal axis of the cylindrical filter element is substantially horizontally aligned when the cylindrical filter element is held by the mounting, and wherein the mounting is configured such that the cylindrical filter element is rotatable about the cylinder longitudinal axis while in the mounting between a first orientation in which the first treatment liquid connector and the second treatment liquid connector face upwards and a second orientation in which the first treatment liquid connector and the second treatment liquid connector face downwards;

the mounting being rotatably attached to the front operating surface of the housing, the mounting being rotatable relative to the front operating surface about a swivel axis, the swivel axis extending orthogonal to the front operating surface of the housing, the swivel axis also extending orthogonal to the cylinder longitudinal axis and through a midsection of the cylindrical filter element when the cylindrical filter element is held by the mounting, the cylindrical filter element being rotatable in the mounting and about the swivel axis between a first angle of inclination in which the cylinder longitudinal axis is horizontal and a second angle of inclination in which the cylinder longitudinal axis is inclined relative to horizontal;

a first flexible line section connecting the first treatment liquid connector to the first housing liquid connector and having a first flexible line length selected to allow the first flexible line section to be connected between the first treatment liquid connector and the first housing liquid connector when the cylindrical filter element is in the first orientation and in the second orientation; and a second flexible line section connecting the second treatment liquid connector to the second housing liquid connector, and having a second flexible line length selected to allow the second flexible line section to be connected between the second treatment liquid connector and the second housing liquid connector when the cylindrical filter element is in the first orientation and in the second orientation.

2. The device according to claim 1, wherein the mounting has at least one horizontally aligned contact surface for the cylindrical filter element.

3. The device according to claim 1, wherein the mounting can be pivoted on the front operating surface about the swivel axis in an angular range $\alpha$ of about $\pm 5°$ about the swivel axis.

4. The device according to claim 1, wherein the mounting can be pivoted on the front operating surface about the swivel axis in an angular range $\alpha$ of about $\pm 2°$ about the horizontal axis.

5. The device according to claim 1, wherein the mounting can be pivoted on the front operating surface about the swivel axis in an angular range $\alpha$ of about $\pm 1°$ about the horizontal axis.

6. The device according to claim 1, wherein the mounting can be pivoted on the front operating surface about the swivel axis in an angular range $\alpha$ of about $\pm 0.5°$ about the horizontal axis.

7. The device according to claim 3, wherein the mounting is coupled to a drive for pivoting the mounting in the angular range $\alpha$ about the swivel axis.

8. The device according to claim 3, wherein the mounting is prestressed in or against a direction of the pivoting by a spring element.

9. The device according to claim 1, wherein the mounting comprises at least one clamping device for holding the cylindrical filter element.

10. The device according to claim 1, further comprising a first blood connector or the first end and a second blood connector for the second end.

11. The device according to claim 1, wherein the housing has a third housing liquid connector and a fourth housing liquid connector, the third housing liquid connector and the fourth housing liquid connector being fluidly connected to each other, and wherein the first flexible line length is selected to allow the first flexible line to connect between the first housing liquid connector and the third housing liquid connector, but not between the first housing liquid connector and the fourth housing liquid connector, and wherein the second flexible line length is selected to allow the second flexible line to connect between the second housing liquid connector and the fourth housing liquid connector, but not between the second housing liquid connector and the third housing liquid connector.

12. The device of claim 1, wherein the cylindrical filter element is a dialyzer.

13. The device according to claim 1, wherein the cylindrical filter element is biased toward the first angle of inclination when the cylindrical filter element is held by the mounting and pivoted about the swivel axis toward the second angle of inclination, so as to always return the cylindrical filter element to a position in which the cylinder longitudinal axis is horizontal.

* * * * *